United States Patent [19]

Huang

[11] Patent Number: 4,901,736

[45] Date of Patent: Feb. 20, 1990

[54] TOILET HAVING URINE TESTER

[76] Inventor: Chuan-Chih Huang, P.O. Box 10160, Taipei, Taiwan

[21] Appl. No.: 202,419

[22] Filed: Jun. 6, 1988

[51] Int. Cl.$^4$ ............................................. A61B 5/00
[52] U.S. Cl. ..................................... 128/760; 128/771
[58] Field of Search ............... 128/760, 771; 4/420; 73/864.21, 864.81–861.85

[56] References Cited

U.S. PATENT DOCUMENTS 3,466,145  9/1969  Duyne .................................. 128/771
3,625,654  12/1971 Duyne .................................. 128/760
4,137,573  2/1979  Kroeger ............................... 128/760
4,554,687  11/1985 Carter et al. ........................ 128/760

Primary Examiner—Max Hindenburg

[57] ABSTRACT

A toilet includes an urine tester having a test tube secured to an operator pivotally mounted in a toilet seat, which can be operatively biased for receiving a urine liquor passed from a toilet user, and for visual detection of possible disease symptoms directly from the tester formed in the toilet for convenient and hygienic self-examination.

5 Claims, 2 Drawing Sheets

TOILET HAVING URINE TESTER

BACKGROUND OF THE INVENTION

When it is intended to measure a specific gravity or to conduct a simple test such as by depositing a test paper in an urine container to detect a symptom of disease, a container or cup must be held by a patient's hand to collect urine for testing, thereby causing inconvenience or even contamination for the patient.

For keeping health purpose, one may detect his or her urine daily to check whether an early symptom is revealed so that an earlier preventive measurement or medical treatment may be taken to preclude the possible disease. Therefore, it is desirably expected to disclose a means for collecting an urine liquor and conduct some simple test directly in a toilet for convenient testing, prevention of urine contamination, and preclusion of dislike odor.

SUMMARY OF THE INVENTION

The object of the present invention is to provide a toilet having an urine tester including an urine collecting tube pivotally secured to a positioning operator, adapted for receiving urine as passed by a toilet user or patient, so that an urine liquor is directly collected in a toilet and tested in situ without contaminating the toilet user for hygienic and convenient purpose.

DETAILED DESCRIPTION

Figure 1:
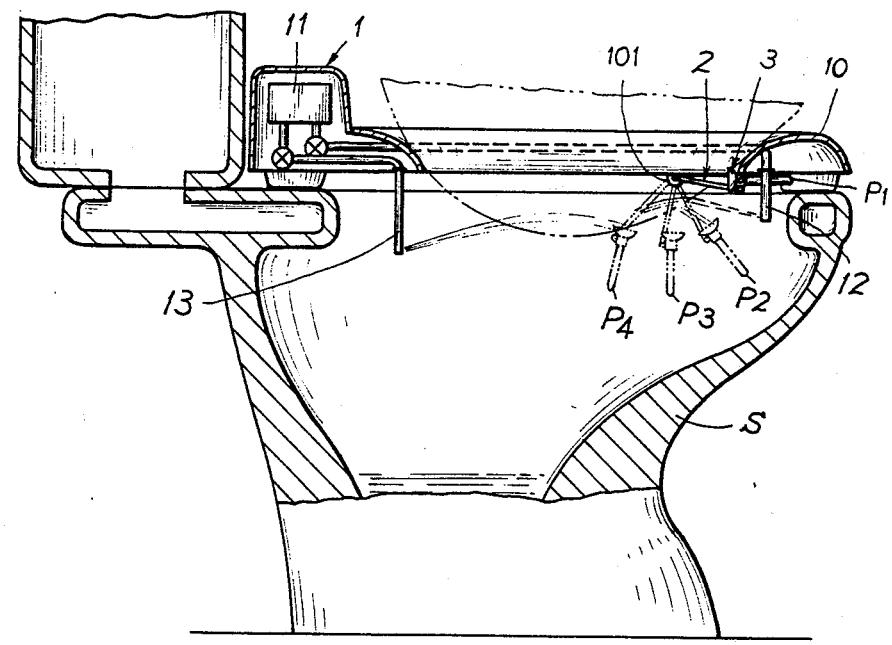
FIG. 1 is a partial sectional illustration of the present invention.

As shown in the figures, the present invention comprises: a toilet 1, a positioning operator 2, and an urine tester 3.

The toilet 1 includes: a toilet seat 10 seating on a toilet bowl S, a warm water supplier 11 having a thermostat for controlling a constant warm water as boosted from the supplier 11, a front nozzle 12 for spraying warm water from the supplier 11 for flushing a user's genitals portion, and a rear nozzle 13 for spraying water from the supplier for flushing a user's anus. Such a toilet for supplying warm water is a conventional toilet device.

The urine tester 3 includes: a test tube 31 made as transparent; a test medium 32 filled in the tube 31 and selected from a plurality of floatable balls of different weights and colors for measuring specific gravity of an urine, a test paper or a test reagent; and a hopper portion 33 connected on an opening of the tube 31. The hopper portion 33 includes a lower skirt portion 331 secured on an upper flange 311 of the tube 31, a plurality of drain holes 332 formed in a bottom portion of the hopper portion 33 fluidically communicated with the test tube 31, a plurality of buffer sticks 333 formed in the hopper portion for preventing the splash of urine drops as impacting on the hopper portion 33, and a lug 334 formed on the skirt portion 331 for mounting the tester 3 on the operator 2.

Figure 3:
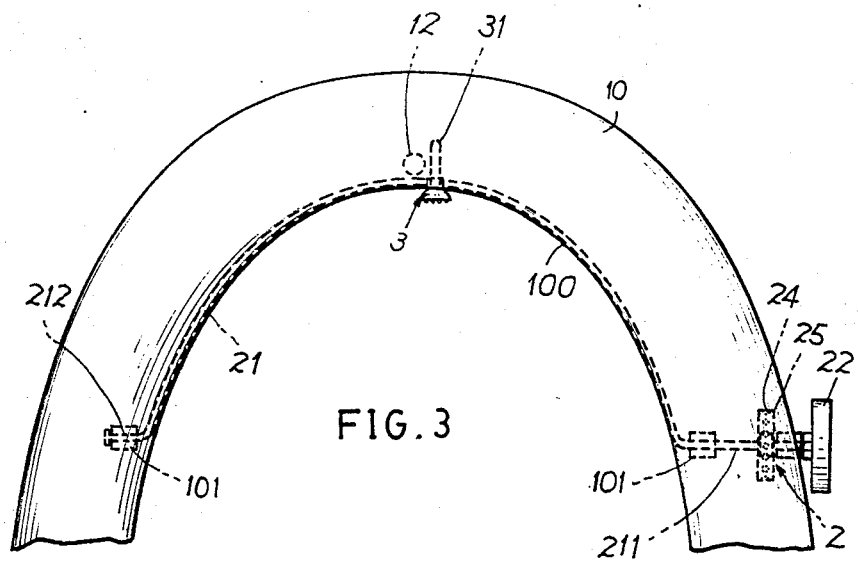
FIG. 3 is a partial top view of the present invention.

The positioning operator 2 includes: a link 21 connecting the tester 3 to normally pose under a front portion of seat 10, a rotating knob 22 secured on a side arm portion 211 of the link 21, and a positioning locker 23 mounted on a toilet seat 10 for selectively biasing the link 21 and the tester 3. The link 21 is formed as an arcuate shape generally coinciding with an inner arcuate edge 100 of the toilet seat 10 as shown in FIG. 3 to have the tester 3 fixed on an apex of the arcuated link 21, having two side arm portions 211, 212 respectively pivotally mounted in two brackets 101 fixed on two lateral opposite sides under the toilet seat 10, in which a first side arm portion 211 is connected with the knob 22 for biasing the link 21. The positioning locker 23 includes a wheel 25 secured on the first side arm portion 211 having a plurality of recesses 24 circumferentially formed on a periphery of the wheel 25, and a locking ball 27 restored by a spring 26 held in the seat 10 resiliently engaging each recess 24 on the wheel 25. The arrangement and structure of the present invention should be designed to be uninfluenced by the bowl S, the seat 10 and the user's body to prevent any obstruction during the biasing operation of the operator 2 and the tester 3.

When using the present invention for detecting a user's urine specimen, the knob 22 can be rotated to bias the test tube 31 downwardly from a horizontal position P1 as shown in FIG. 1 to a tilting position P2 for orienting the tube opening upwardly leftwardly for receiving an urine liquor passed by the user. Then, the tube 31 is biased to be vertically pendant (P3) for detecting the specific gravity or other properties of the urine by visual way.

The tube 31 is then further biased to orient the tube opening for receiving a water stream as sprayed from either nozzle 13 or 12 for cleaning the tube 31. Finally, the tube 31 is biased to decant the residual water or urine (P5) as shown in dotted line of FIG. 2.

Figure 4:
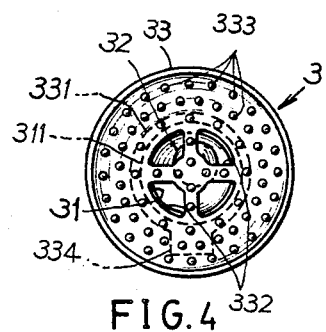
FIG. 4 is a top view illustration of the urine tester of the present invention.

The size of each drain hole 332 should be smaller than the size of the test medium 32 such as a diameter of the ball as shown in FIG. 4, to prevent escape of the medium 32 during testing operation.

Other modifications can be made for the operator 2 of the present invention by those skill in the art. The hopper portion 33 may be made of elastomer materials for easy securing on the tube 31 or removal therefrom.

The present invention has the following advantages superior to a conventional urine tester such as a pipette sucking an urine liquor from a portable cup:

1. The urine is directly passed into the test tube without contacting the user's hand for hygienic and convenient self-examination.

2. Since the test tube is formed in a toilet and the test can be directly done in situ in the toilet, someone may not forget a daily detection as his or her daily seating on the toilet seat provided with the present tester may always remind him or her for such a daily detection.

3. The link 21 carrying the test tube 31 is pivotally secured on the toilet seat and the knob 22 can be optionally rotated to bias the link 21 to pose the tube 31 for collecting urine sample for testing, for flushing the tube after testing, or for normally storing the tube beneath the seat, for convenient operation, maintenance and storage.

Figure 2:
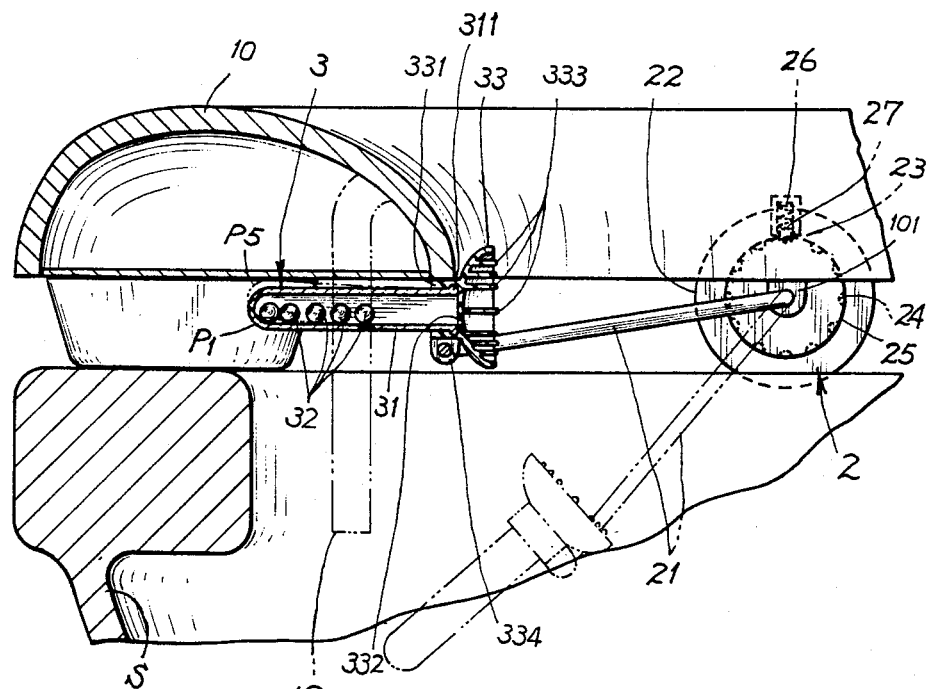
FIG. 2 is an illustration of the present invention enlarged from FIG. 1.

4. The tester and the link is selectively locked at any desired position by resiliently engaging the ball 27 with wheel recess 24 as shown in FIG. 2 of the tester.

I claim:

1. A toilet having urine tester comprising:

a toilet seat seating on a toilet bowl, a warm water supplier for supplying warm water, a front nozzle for spraying warm water supplier from said supplier for flushing a user's genitals portion and a rear nozzle for spraying water from said supplier for flushing a user's anus;

a urine tester having a test medium stored therein, said test medium being selected from a plurality of floatable balls of different weights and colors for measuring specific gravity of an urine as filled in said tester, or a test paper, or a test reagent for visual detection of some disease symptoms directly from the tester; and a positioning operator pivotally securing said tester on the toilet seat for operatively biasing said tester for receiving urine as passed from a user into said tester, or for positioning the tester for detection, or for flushing the tester as water-sprayed by said nozzles, the improvement which comprises:

said urine tester including a test tube having the test medium filled therein, and a hopper portion secured on an opening of the tube, said hopper having a plurality of drain holes formed in a bottom of said hopper portion for passing a collected urine liquor through said drain holes into said tube, and having a lug for connecting said positioning operator; and said positioning operator including a link connecting the lug of said tester to normally pose said tester under a front portion of said toilet seat, a rotating knob secured on a side arm portion of said link, and a positioning locker mounted on the toilet seat for selectively biasing said link and said tester for testing or flushing operations.

2. A toilet having urine tester according to claim 1, wherein said hopper portion of said urine tester comprises a plurality of buffer sticks formed in said hopper portion for the buffer of an impacting urine stream filling into the tester.

3. A toilet having urine tester according to claim 1, wherein said link of said positioning operator is formed as an arcuate shape generally coinciding with an inner arcuate edge of said toilet seat to have the tester fixed on an apex of said arcuate link, and having two side arm portions respectively pivotally secured in two brackets fixed on two lateral opposite sides under the toilet seat.

4. A toilet having urine tester according to claim 1, wherein said positioning locker of said positioning operator comprises a wheel secured on said first side arm portion having a plurality of recesses circumferentially formed on a periphery of said wheel, a locking ball restored by a spring held in said toilet seat resiliently engaging each said recess fromed on said wheel, whereby upon a rotation of the rotating knob to drive said wheel to operatively bias said link carrying said tester, said tester is locked at a desired position by resiliently engaging said ball with said recess of said wheel.

5. A toilet having urine tester according to claim 1 wherein said urine tester is a tester for testing specific gravity of a user's urine.

* * * * *